United States Patent [19]

Jensen et al.

[11] Patent Number: 4,752,583
[45] Date of Patent: Jun. 21, 1988

[54] MONOCLONAL ANTIBODIES TO HUMAN HEMOGLOBIN S AND CELL LINES FOR THE PRODUCTION THEREOF

[75] Inventors: Ronald H. Jensen, Livermore; Martin Vanderlaan, San Ramon; William L. Bigbee; Larry H. Stanker, both of Livermore; Elbert W. Branscomb, Walnut Creek; Robert J. Grabske, Berkeley, all of Calif.

[73] Assignee: The United States of America as represented by the United States Department of Energy, Washington, D.C.

[21] Appl. No.: 676,162

[22] Filed: Nov. 29, 1984

[51] Int. Cl.$^4$ .................. C12N 5/00; C07K 15/04
[52] U.S. Cl. .................. 435/240.27; 435/7; 435/68; 435/70; 435/172.2; 935/104; 935/110; 436/548; 530/387
[58] Field of Search .................. 266/112 R, 112.5 R; 424/85; 435/4, 7, 28, 68, 70, 172.2, 240, 188, 172.1, 948; 935/95, 99, 100, 102–104, 110; 436/513, 514–516, 518, 528–532, 536–542, 543–548, 15, 63, 66, 800, 804, 811, 815, 822, 823

[56] References Cited

PUBLICATIONS

Klasen, E. A. et al., Journal of Immunological Methods, 54:241–250 (1982).
Klasen, E. A. et al., Journal of Immunological Methods, 59:281–287 (1983).
Sullivan, T. T. et al., Journal of Immunogenetics, 10:69–82 (1983).
Stamatoyannopoulos, G. et al., Blood 61:(3):530–539 (1983).
Papayannopoulou, T. C. et al., British Journal of Haematology, 34, 25 (1976).
Stamatoyannopoulos, G. et al., The Lancet, Oct. 31, 1981.
Jensen, R. H. et al., UCRL-88226, Lawrence Livermore National Laboratory, Jan. 23, 1983.
Stanker, L. H. et al., Hykridoma 3:105 (1984).
Bigbee, W. L. et al., *Individual Susceptibility to Genotoxic Agents in the Human Population*, de Serres, F. et al., eds., Plenum Publishing Co. (1984), pp. 249–266.
Jensen, R. H. et al., *Biological Dosimetry*, Eisert, W. G. et al. eds., Springer-Verlag, Berlin (1984), pp. 161–170.

Primary Examiner—Margaret Moskowitz
Attorney, Agent, or Firm—Shyamala T. Rajendar; L. E. Carnahan; Judson R. Hightower

[57] ABSTRACT

The present invention provides monoclonal antibodies specific to and distinguish between hemoglobin S and hemoglobin A and methods for their production and use. These antibodies are capable of distinguishing between two hemoglobin types which differ from each other by only a single amino acid residue. The antibodies produced according to the present method are useful as immunofluorescent markers to enumerate circulating red blood cells which have the property of altered expression of the hemoglobin gene due to somatic mutation in stem cells. Such a measurement is contemplated as an assay for in vivo cellular somatic mutations in humans. Since the monoclonal antibodies produced in accordance with the instant invention exhibit a high degree of specificity to and greater affinity for hemoglobin S, they are suitable for labeling human red blood cells for flow cytometric detection of hemoglobin genotype.

5 Claims, 3 Drawing Sheets

MONOCLONAL ANTIBODIES TO HUMAN HEMOGLOBIN S AND CELL LINES FOR THE PRODUCTION THEREOF

The United States Government has rights in this invention pursuant to Contract No. W-7405-ENG-48 between the University of California and the United States Department of Energy.

The subject invention is related generally to monoclonal antibodies and more specifically to monoclonal antibodies to human hemoglobins.

ABBREVIATIONS

Abbreviations or definitions used in the disclosure herein are as follows:

Hb-A - normal human hemoglobin; Hb-S - sickle cell human hemoglobin type; ELISA - enzyme linked immunosorbent assay; HuS-1 - hybridoma that secretes monoclonal antibodies specific to Hb-S or the monoclonal antibodies so secreted; HuS-2 - a hybridoma that secretes monoclonal antibodies to Hb-S or the monoclonal antibodies so secreted; ABTS - 2,2 azino-di-(3-ethylbenzthiazoline sulfonic acid; BSA - bovine serum albumin; BTG - bovine thyroglobulin; MBS - maleimidobenzoyl-hydroxylsuccinic acid; D-aspartic acid; E - glutamic acid; Y - tyrosine; N - asparagine; Q - glutamine; S - serine; T - threonine; C - cysteine; H - histidine; K - lysine; R - arginine; G - glycine; A - alanine; w - tryptophan; F - phenylalanine; V - valine; L - leucine; I - isoleucine; M - methionine; P - proline.

BACKGROUND OF THE INVENTION

In recent times, there has been considerable research, clinical and commercial activity in the production and use of monoclonal antibodies for diagnostic and therapeutic purposes. Although the general technique of the fusion of spleen cells with myeloma cells was published by Kohler and Milstein in 1975, the production of monoclonal antibodies to specific antigens is still fraught with difficulties, especially where the antibodies must recognize and be able to distinguish between closely related antigens. Some variations of protein antigens differ from each other by a single amino acid residue, as is the case with many hemoglobin variants. Monoclonal antibodies directed to these protein antigens must be able to recognize and distinguish these proteins from each other on the basis of a single amino acid difference.

Human hemoglobin (Hb) is a protein about which a great deal of structural and functional information has become available. There are more than four hundred mutants or variants of hemoglobin known. Most of these variants differ from normal hemoglobin, hemoglobin A (Hb-A) by a single amino acio substitution. Human hemoglobin variants such as, for example, sickle-cell hemoglobin or hemoglobin S (Hb-S), as it is known in the art, and hemoglobin C (Hb-C) differ from normal hemoglobin A (Hb-A) by a single amino acid substitution at the sixth amino acid residue of the β-globin chain. In Hb-S, valine is substituted for glutamic acid and in Hb-C, lysine is substituted for glutamic acid. These amino acid substitutions occur as tne result of single base changes in the globin gene of normal Hb-A. Efforts have been made to devise metnods which would identify and distinguish these variants from the normal protein.

Th. Papayannopoulou, T. C. McGuire, G. Lim, E. Garzel, P. E. Nute and G. Stamatoyannopoulos, in an article entitled "Identification Of Haemoglobin S In Red Cells And Normoblasts, Using Fluorescent Anti-Hb S Antibodies", (Brit. J. Haemat., 34, 25 (1976)) described procedures for the preparation of horse polyclonal antibodies monospecific for Hb-S and their use in detecting Hb-S in red cells and erythroid precursors.

G. Stamatoyannopoulos, D. Lindsley, Th. Papayannopoulou, M. Farquhar, M. Brice, and P. E. Nute, G. R. Serjeant and H. Lehmann, "Mapping Of Antigenic Sites On Human Haemoglobin By Means Of Monoclonal Antibodies And Haemoglobin Variants", The Lancet, Oct. 31, 1981, discloses the usefulness of variant hemoglobins in defining antigenic sites recognized by anti-globin monoclonal antibodies.

R. H. Jensen, W. Bigbee and E. W. Branscomb, in "Somatic Mutations Detected By Immunofluorescence And Flow Cytometry", (UCRL-88226, Lawrence Livermore National Laboratory, Livermore, Calif., Jan. 23, 1983) disclose immunofluorescence and flow cytometric techniques for the detection of certain somatic cell mutations, using both monoclonal and polyclonal antibodies.

The immunofluorescence and flow cytometric techniques disclosed by Jensen et al., (UCRL-88226), are based on a single-cell detection system for studying somatic cell mutations. The hemoglobin system, among several biochemical genetic systems in. man, offers the best possibilities for use in these studies for various reasons. In addition to a great deal of structural and functional information about hemoglobin being readily available, and the easy availability of hemoglobin in large enough quantities for research purposes, ninety-five percent of the protein in erythrocytes is Hb, and about 20 to 50 percent of the protein per cell is abnormal in the case of most heterozygous structural mutations of the globin gene. Over 350 of hemoglobin mutational variants have been structurally characterized and are thus available for further mutation research. Most of these exhibit single amino acid substitutions indicating single base substitutions, although double substitutions, amino acid deletions, amino acid insertions and variants with elongated or shortened polypeptide chains are known. Most of these Hb variants are postulated to exist at very low frequencies in circulating red cells of every genetically normal individual. Furthermore, mature erythrocytes lend themselves very satisfactorily to single cell assays. They are easily obtained in large numbers and can be readily analyzed in suspension and express mutations that occur in the erythroid progenitors.

It would, therefore, be highly desirable to have an assay or method for the detection of heterozygous normal/mutant cells, i.e., cells which contain co-dominantly expressed genes in which one allele is normal and the other is mutant. Alleles are alternative forms of an individual gene. Such cells should produce both normal and mutant gene products in the case of neutral mutations and proteins coded for by only one allele in the case of "null" mutations. A "null" mutation is a single mutational event resulting in the lack of a functional gene product. Such a method could be either a clonogenic assay of mutant cells or an immunologic detection of cells which contain mutant gene products.

SUMMARY OF THE INVENTION

Accordingly, it is an object of the present invention to provide an assay for somatic cell mutations which occur in vivo.

Another object is to provide for the sensitive detection of sickle cell trait in prenatal and neonatal individuals.

A further object is to provide for the specific differentiation among several hemoglobin mutational variants.

Yet another object is to provide a method for distinguishing between hemoglobin A and hemoglobin S.

Still another object is to provide for the detection of sickle cell trait in susceptible populations.

Additional objects, advantages and novel features of the invention will be set forth in part in the description which follows, and in part will become apparent to those skilled in the art upon examination of the following and the accompanying drawings and their descriptions which form part of the disclosure herein and are incorporated herein by reference, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the subject invention is directed to the production of monoclonal antibodies to human hemoglobin, more specifically, to sickle cell hemoglobin or hemoglobin S (Hb-S). The present invention also provides a method for the production and use of monoclonal antibodies to protein or peptide antigens selected from the group consisting of human hemoglobin S, the β-globin chain of Hb-S, a synthetic analog thereof conjugated or unconjugated to an immunogenic carrier protein, a fragment of the β-globin chain corresponding to the amino terminus thereof and a synthetic analog of said fragment conjugated or unconjugated to an immunogenic carrier protein, and hybrid cell lines capable of continuously producing these antibodies.

The method for the production of monoclonal antibodies to Hb-S in accordance with the subject invention, comprises immunizing a suitable animal with a protein or peptide antigens selected from the group consisting of human hemoglobin S molecule, the β-globin chain of Hb-S, a synthetic analog thereof conjugated or unconjugated to a carrier protein, a fragment of the β-globin chain corresponding to the amino terminus thereof and a synthetic analog of said fragment conjugated or unconjugated to a carrier protein, obtaining from the animal sensitized spleen cells or lymphocytes capable of producing antibodies to the antigen of choice, fusing the sensitized spleen cells with myeloma cells of the same species or of another animal species, culturing the hybrid cells in a suitable host or in a culture medium, isolating clones of hybrid cells (hybridomas) which continuously produce specific antibodies to the antigen, selecting hybridomas which produce these monoclonal antibodies, producing these antibodies in the culture medium or in a host and harvesting the antibodies from the culture medium or from the host used for growing the cells.

According to a further aspect of the present invention, in accordance with its objects and purposes, the cell lines developed in accordance with the instant invention are capable of producing highly specific monoclonal antibodies which distinguish Hb-S from normal hemoglobin, Hb-A.

The present invention also provides an improved method for distinguishing between the two hemoglobins, Hb-S and Hb-A. The method is contemplated to be useful for the sensitive detection of sickle cell trait in prenatals, neonatals, children and adults. Quantitation of the sickle cell trait allows distinction between homozygous SS and neterozygous AS individuals. These antibodies are also contemplated to be useful in the identification of somatic cell mutations in red cells of normal, homozygous AA individuals. More specifically, the subject method for differentiating between hemoglobin S and hemoglobin A, by use of the specific monoclonal antibodies produced according to the instant method and which monoclonal antibodies are capable of distinguishing between hemoglobin S and hemoglobin A, comprises immunizing a first species of an animal, preferably mice, rats, hamsters, rabbits and the like, still more preferably mice and rats, with a protein or peptide antigen selected from the group consisting of human hemoglobin S, the β-globin chain of Hb-S, a synthetic analog thereof conjugated or unconjugated to an immunogenic carrier protein, a fragment of the β-globin chain corresponding to the amino terminus thereof and a synthetic analog of said fragment conjugated or unconjugated to an immunogenic carrier protein, by repeated administrations of the antigen in a suitable amount, generally between about 20 ug to about 100 ug, preferably about 50 ug, per animal, per administration, at intervals of about one to four weeks, preferably about one to two weeks; removing from the animal sensitized spleen cells which are now capable of producing antibodies to the antigen; fusing the sensitized spleen cells to myeloma cells of the first species of animal or of another animal species to produce hybrid cells; culturing tne hybrid cells so produced; isolating clones of the hybrid cells which continuously produce monoclonal antibodies specific to the antigen and/or to Hb-S; selecting hybridomas that produce monoclonal antibodies which distinguish between Hb-S and Hb-A; producing and identifying tnese monoclonal antibodies; isolating and purifying the monoclonal antibodies if preferred; and assaying blood samples for the presence of Hb-S with the monoclonal antibodies. The monoclonal antibodies produced in accordance with the instant invention may be used in the form of hybridoma supernatant or ascites fluid or isolated and purified antibodies, depending on the contemplated use.

The antibodies produced according to the present method also have applications as immunofluorescent markers which can be used to enumerate circulating red blood cells which have the property of altered expression of tne hemoglobin gene due to somatic mutation in stem cells. Such a measurement is contemplated as an assay for in vivo cellular somatic mutations in humans. These monoclonal antibodies are able to distinguish between two nemoglobin variants, specifically Hb-A and Hb-S, that differ from each other by only a single amino acid. These antibodies produced in accordance with the instant invention exhibit a high degree of specificity to and greater affinity for hemoglobin S and are suitable for labeling human red blood cells for flow cytometric detection of hemoglobin genotype and for other uses as described herein.

These drawings form part of the specification and are incorporated herein by reference.

DETAILED DESCRIPTION OF THE DRAWINGS

Figure 1A:
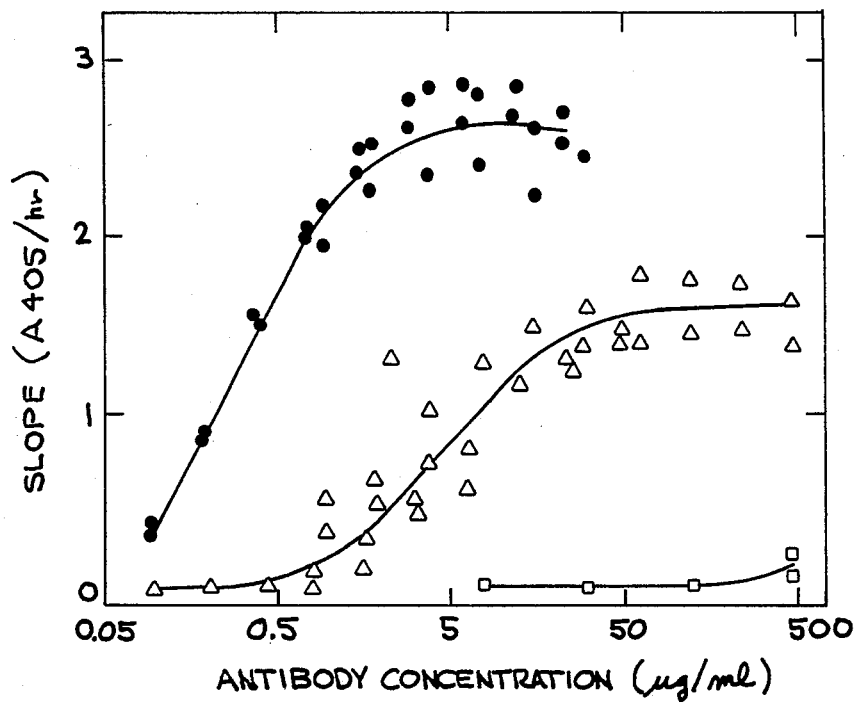
FIG. 1a is graph showing the binding of monoclonal antibodies produced by the hybridoma designated as HuS-1 to VHLTPVEKSAVTYC-BSA and VHLTPEEKSAVTYC-BSA, as a plot of antibody concentration vs. relative ELISA response.
Figure 1B:
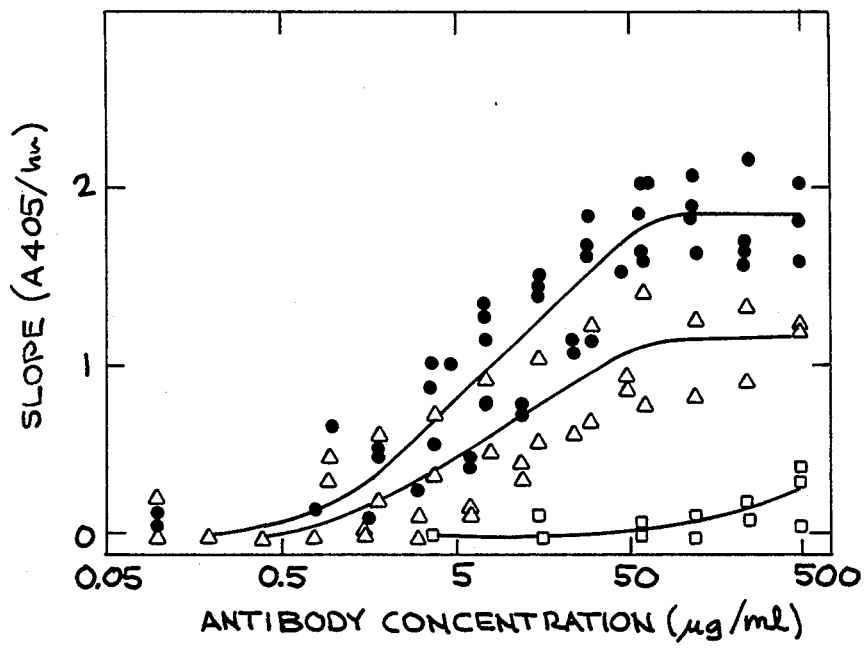
FIG. 1b is another graph showing tne binding of monoclonal antibodies produced by the hybridoma designated as HuS-1 with homozygous Hb-SS, Hb-AA and heterozygous Hb-AS in terms of antibody vs. relative ELISA response.

FIGS. 1a and 1b show enzyme linked immunosorbent assays (ELISA) with HuS-1. ELISAs were performed according to known methods except that tne secondary antibody used was peroxidase-conjugated goat anti-mouse immunoglobulin, purchased from United States Biochemical Corporation, Cleveland, Ohio and the substrate used for the enzyme was 0.3 mM solution of $H_2O_2$, 0.8 mM ABTS (2,2 azino-di-(3-ethylbenzthiazoline sulfonic acid) in 0.1 M sodium citrate buffer pH 5.5. Slopes were measured using an automated computer based enzyme assay system. Antigens attached to the microtiter plates were 0.1 ml aliquots of 20 ug/ml of VHLTPVEKSAVTYC-BSA, VHLTPEEKSAVTYC-BSA, BSA, BTG and BSA-MBS (FIG. 1a); and 100 ug/ml of Hb-S, Hb-AS, and Hb-A (FIG. 1b). 50 ul of antibody at the concentrations shown on the abscissa were added to each well. Similar ELISAs using 24 other human hemoglobin variants containing different single amino acid substitutions than Hb-S and also on 7 primate hemoglobins containing multiple amino acid substitutions different from Hb-S. All these titrations showed that the reactivity of HuS-1 with these various hemoglobins was either equal to or less than that with Hb-A.

Figure 2A:
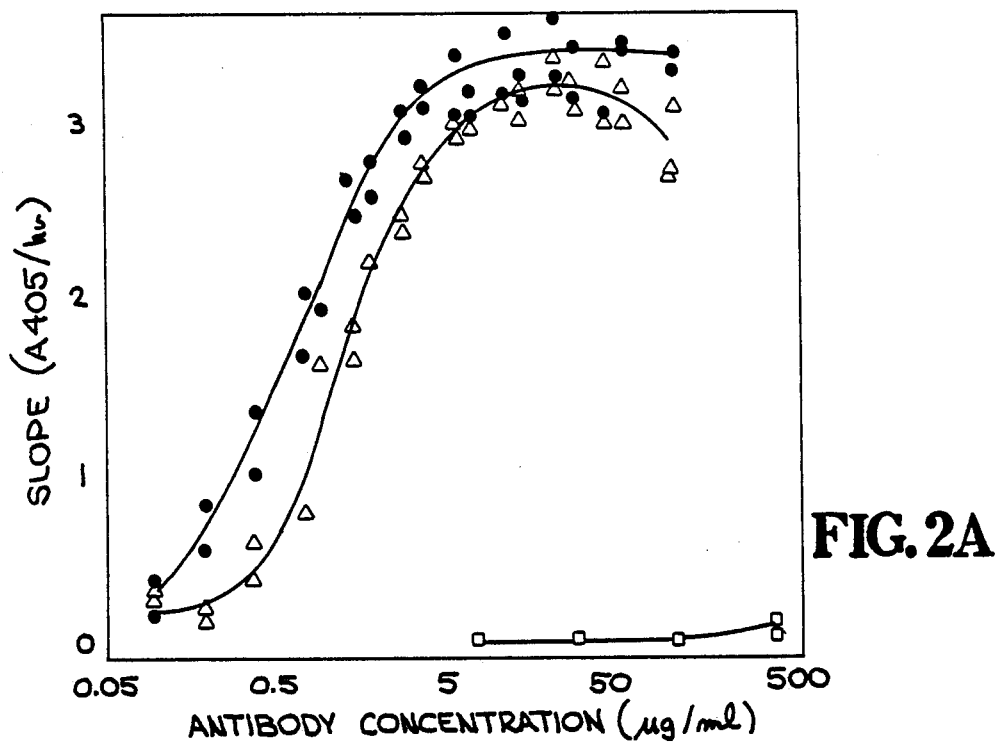
FIG. 2a is graph showing the binding of monoclonal antibodies produced by the hybridoma designated as HuS-2 to VHLTPVEKSAVTYC-BSA and VHLTPEEKSAVTYC-BSA, as a plot of antibody concentration vs. relative ELISA response.
Figure 2B:
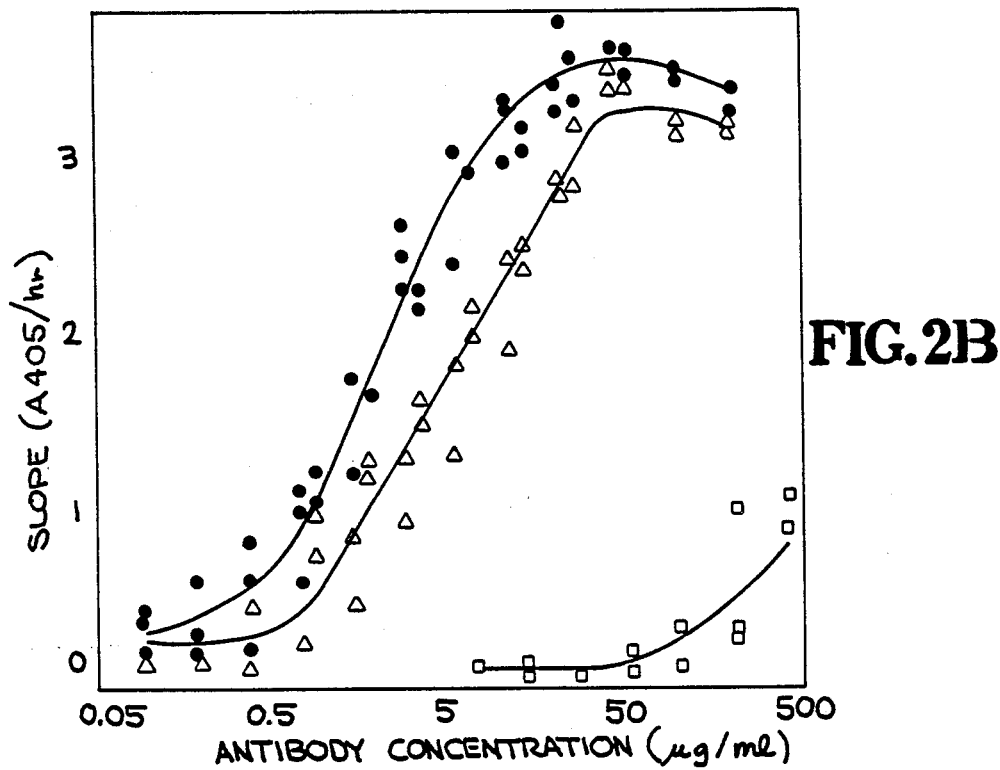
FIG. 2b is another graph showing the binding of monoclonal antibodies produced by the hybridoma designated as HuS-2 with homozygous Hb-SS, Hb-AA and heterozygous Hb-AS in terms of antibody vs. relative ELISA response.

FIG. 2, similarly, shows ELISA results with HuS-2. ELISAs were performed in the same manner as with HuS-1. Antigens attached to the microtiter plastic plates were 0.1 ml aliquots of 20 ug/ml of VHLTPVEKSAVTYC-BSA, VHLTPEEKSAVTYC-BSA, BSA, BTG and BSA-MBS (FIG. 2a); and 100 ug/ml of Hb-S, Hb-AS, and Hb-A (FIG. 2b). Titrations of HuS-2 against the other 24 human and 7 primate hemoglobins showed that the reactivity of HuS-2 with all these hemoglobins was equal to or less than that with Hb-A.

Figure 3:
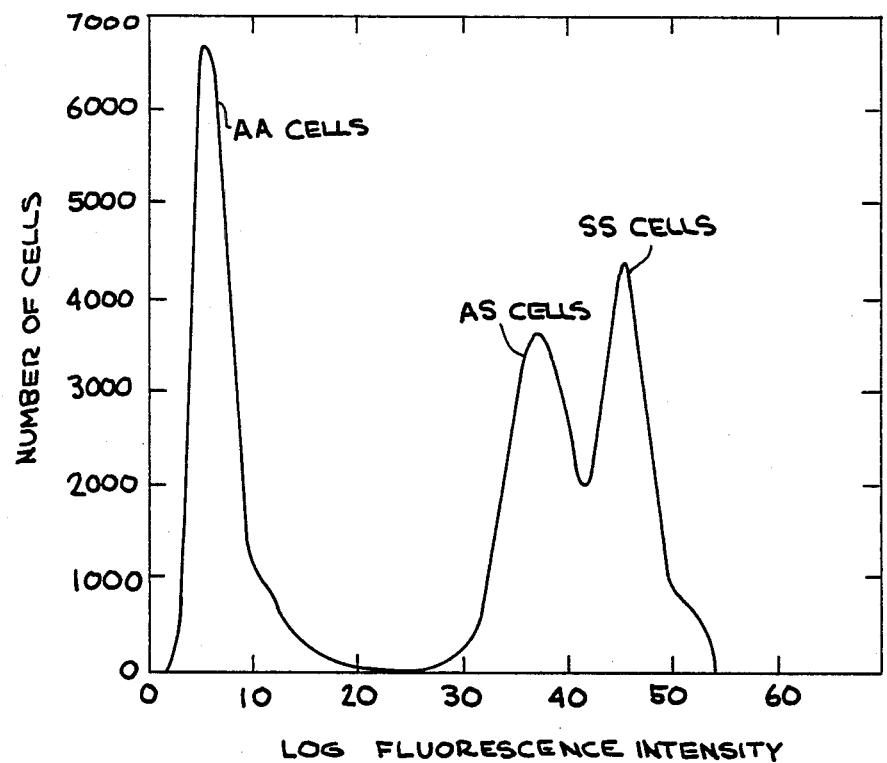
FIG. 3 is a flow cytometric diagram showing the competitive binding of monoclonal antibodies produced by the hybridomas designated as HuS-1 to Hb-S in homozygous SS cells and heterozygous AS cells in the presence of homozygous AA cells.

FIG. 3 shows a pattern of flow cytometry of erythrocytes labeled with HuS-1 and fluoresceinated goat anti-mouse immunoglobulin secondary antibody. Excitation was at 488 nm. Signals were collected and amplified with a logarithmic amplifier such that 7.5 channels on the abscissa equals a doubling of fluorescence intensity.

Figure 4:
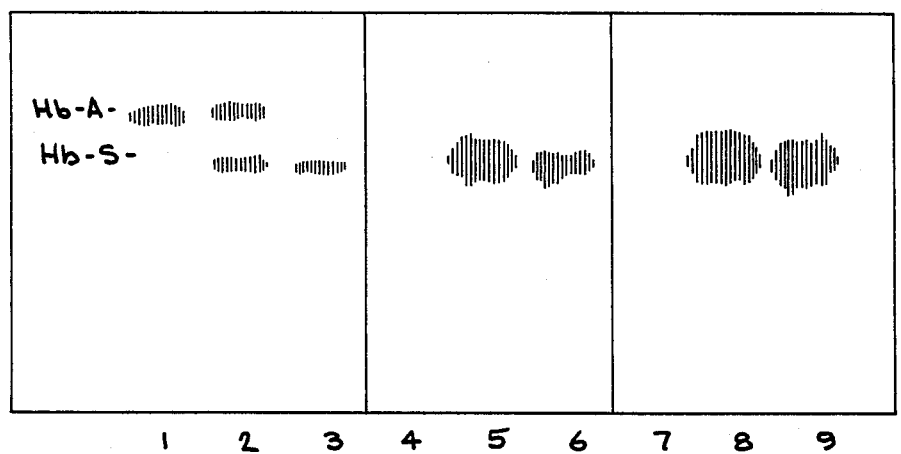
FIG. 4 shows the electrophoresis pattern of Hb-A and Hb-S immunostained with monoclonal antibodies produced by the hybridomas designated as HuS-1 and HuS-2.

FIG. 4 shows the reactivity of HuS-1 and HuS-2 with human hemoglobin on electrophoresis gel. The hemoglobins were electrophoresed on a gel slab of Paragon gel, obtained from Beckman Instruments, Palo Alto, Calif., and fixed with acetic acid-methanol. Lanes 1, 4, and 7 show the gel pattern for Hb-A, lanes 2, 5 and 8 show the electrophoretic pattern of Hb-AS, and lanes 3, 6 and 9 show the electrophoretic pattern of Hb-S. Part of tne gel, shown in lanes 1–3, was stained with Serva Blue and the remainder was incubated with HuS-1 (lanes 4–6) or with HuS-2 (lanes 7–9), washed, incubated with peroxidase-conjugated goat anti-mouse immunoglobulins, washed, and incubated with 4-chloro, 1-naphthol substrate.

DETAILED DESCRIPTION OF THE INVENTION

The subject invention is directed to the production of monoclonal antibodies to human hemoglobin, more specifically, to sickle cell hemoglobin or hemoglobin S (Hb-S). The present invention also provides a method for the production and use of monoclonal antibodies to a protein or peptide antigen selected from the group consisting of human hemoglobin S, the β-globin chain of Hb-S, a synthetic analog thereof conjugated or unconjugated to an immunogenic carrier protein, a fragment of the β-globin chain and a synthetic analog of said fragment conjugated or unconjugated to an immunogenic carrier protein and hybrid cell lines capable of continuously producing these antibodies.

The method for the production of monoclonal antibodies to Hb-S in accordance with the subject invention, comprises immunizing a suitable animal, preferably mice, rats, hamsters and rabbits, still more preferably mice, with a protein or peptide antigen selected from the group consisting of human hemoglobin S antigen, the β-globin chain of Hb-S, a synthetic analog thereof conjugated or unconjugated to an immunogenic carrier protein, a fragment of the β-globin chain and a synthetic analog of said fragment conjugated or unconjugated to an immunogenic carrier protein, preferably a fragment corresponding to the amino terminus of said β-globin chain conjugated or unconjugated to a carrier protein, obtaining from the animal sensitized spleen cells or lymphocytes capable of producing antibodies to the antigen of choice, fusing the sensitized spleen cells with myeloma cells of the same species or of another animal species, culturing the hybrid cells in a suitable host or in a culture medium, isolating clones of hybrid cells (hybridomas) which continuously produce or secrete specific antibodies to the antigen, selecting hybridomas that produce monoclonal antibodies specific to the selected antigen; producing and identifying these monoclonal antibodies; harvesting the antibodies from the culture medium or from the host used for growing the cells; and isolating and purifying the monoclonal antibodies if preferred.

According to a further aspect of the present invention, in accordance with its objects and purposes, the cell lines, designated as HuS-1 and HuS-2, developed in accordance with the instant invention are capable of producing highly specific monoclonal antibodies which distinguish Hb-S from normal hemoglobin, Hb-A.

The present invention also provides an improved method for distinguishing between the two hemoglobins, Hb-S and Hb-A. The method is contemplated to be useful for the sensitive detection of sickle cell trait in prenatals, neonatals, children and adults. Quantitation of the sickle cell trait allows distinction between homozygous SS and heterozygous AS individuals. These antibodies are also contemplated to be useful in the identification of somatic cell mutations in red cells of normal, homozygous AA individuals. More specifically, the subject method for differentiating between hemoglobin S and hemoglobin A, by use of the specific monoclonal antibodies produced according to the instant method and which monoclonal antibodies are capable of distinguishing between said hemoglobin S and hemoglobin A, comprises immunizing a first species of an animal, with a protein or peptide antigen selected from the group consisting of human hemoglobin S antigen, the β-globin chain of Hb-S, a synthetic analog thereof conjugated or unconjugated to an immunogenic carrier protein, a fragment of the β-globin chain and a synthetic analog of said fragment conjugated or unconjugated to a known immunogen or to a carrier protein which is a known immunogen, preferably a fragment corresponding to the amino terminus of said β-globin chain conjugated or unconjugated to a known immunogen or to a carrier protein which is a known immunogen, by repeated administrations of the antigen in a suitable amount, generally between about 20 ug to about 100 ug, preferably about 50 ug, per animal, per administration, at intervals of about one to four weeks, preferably one to two weeks; removing from the animal sensitized spleen cells which are now capable of producing antibodies to the antigen; fusing the sensitized spleen cells to myeloma cells of the first species of animal or of another animal species to produce hybrid cells; culturing the hybrid cells so produced; isolating clones of the hybrid cells which continuously secrete monoclonal antibodies specific to the antigen and/or to Hb-S; selecting hybridomas which produce the monoclonal antibodies which distinguish between Hb-S and Hb-A; producing these monoclonal antibodies and isolating them if necessary; and assaying blood samples for the presence of Hb-S with the monoclonal antibodies so produced. The hybridomas may be propagated in a suitable host animal or grown in a suitable culture or carrier medium. Host animals include but are not limited to mice, rats, hamsters, guinea pigs, rabbits and the like. Suitable culture or carrier media include but are not limited to physiological saline, HEPES buffer, Hank's solution, Ringer's solution, Dulbecco's medium, modified or otherwise, Eagle's medium, modified or otherwise, and the like. As used herein, such carrier or culture media includes ascites fluid and hybridoma supernatant other than one of the culture media specified above.

Techniques for the immunization of laboratory animals with synthetic peptides which are analogs of protein fragments and identifying specific protein epitopes, which are immunologically recognized features of a protein, as represented by these synthetic peptides, which trigger the production of antibodies, are known to those skilled in tne art. When these peptides fail to produce an adequate immune reaction by themselves, they are usually conjugated to a known immunogen or to a carrier protein whicn is a known immunogen. By the use of this peptide-protein conjugate, the peptide is rendered immunogenic. Antibodies produced in response to this immunogenic conjugate recognize the peptide apart from the carrier protein. Carrier proteins may be selected from any group of proteins which are immunogenic. Suitable carrier proteins include but are not limited to serum albumins, globulins including thyroglobulins and the like. Bovine or human serum albumin, and bovine or human thyroglobulin are conveniently employed. The antibodies of the subject invention may be used in the form of hybridoma supernatant, or as ascites fluid or as the isolated and purified monoclonal antibodies.

The following examples, presented by way of illustration, serve to explain the present invention in more detail. These examples are not to be construed as limiting the invention to the precise forms or modes disclosed. In fact, several improvements and modifications are possible. It is intended that such improvements and modifications are encompassed by the appended claims.

EXAMPLE 1

Immunization Of Mice With The Antigen

A synthetic dodecapeptide, VHLTPVEKSAVT, that is identical to the amino terminal sequence of the β-globin chain of Hb-S was purchased from Peninsula Labs, Belmont, Calif., and systematically tested as an immunogen by intramuscular injections of 50 ug of this peptide into twelve mice over a six month period. Other peptides corresponding to other epitopes on the β-globin chain of Hb-S or otner Hb variants may also be used effectively in these procedures. Six of these mice were Balb/c mice and six were highly immunoresponsive Biozzi High Responder mice. ELISAs of the sera from these mice. after one to six months of bi-weekly injections showed no reactivity either with the immunogen or with Hb-S. In order to increase immunogenicity, the peptide VHLTPVEKSAVTYC, whicn was extended from the Hb-S terminal sequence by a tyrosine and cysteine residue, to facilitate specific radioiodination and conjugation at the carboxyl terminus to an immunogenic carrier protein. Using maleimidobenzoyl-hydroxylsuccinic acid (MBS), this extended peptide was conjugated to a carrier protein such as bovine thyroglobulin (BTG). Edman degradation of the resulting conjugate indicated that 20 peptide moieties were attached to each BTG molecule. This peptide-BTG conjugate served as an effective immunogen. All mice immunized with this peptide-BTG conjugate (6 Balb/c, 6 Biozzi and 6 C57/black) showed high serum titers against the peptide conjugated with MBS to bovine serun albumin (VHLTPVEKSAVTYC-BSA) and against native hemoglobins. Two of the mice (both Balb/c) showed serum reactions that were much stronger against Hb-S than against Hb-A. Although Balb/c, Biozzi and C57/black mice were used in these experiments, other strains of mice or other similar animal species may be substituted. Such substitutions are contemplated to be within the scope of these experiments.

EXAMPLE 2

Preparation Of HuS-1 and HuS-2

Spleens from several of the immunized mice were removed and the spleen cells were fused with SP2/0 mouse myeloma cells. Although SP2/0 myeloma cells were conveniently used, the fusion is not limited to the use of SP2/0 myeloma cells and the use of other myeloma cells is contemplated to be within the scope of these experiments. The fusion resulted in the growth of hybridomas which secreted antibodies reactive with the peptide-BSA conjugate. Using multiple enzyme-linked immunosorbent assays (ELISA) against three antigens, VHLTPVEKSAVTYC-BSA, Hb-A and Hb-S, a number of hybridomas which produced antibodies specific for the peptide conjugate and for Hb-S were selected. From one fusion, two stable hybridomas, designated as HuS-1 and HuS-2 and which produced monoclonal antibodies that could discriminate between Hb-S and Hb-A, were isolated. Each hybridoma was grown in ascites and was purified by column chromatography using hydroxylapatite. The purified components were found to be greater than 95% pure as determined by SDS-polyacrylamide gel electrophoresis. Isotype analysis of these purified antibodies showed that HuS-1 is IgG2b and HuS-2 is IgA. Both antibodies contained kappa light chains. Hybridomas referred to herein as HuS-1 and HuS-2 are on deposit with the American Type Culture Collection, 12301 Parklawn Drive, Rockville, Md. 20252, under the Budapest Treaty, and are assigned ATCC Accession Nos. HB-8660 and HB-8661 respectively. As used herein, HuS-1 and HuS-2 refer to either tne hybridomas which produce monoclonal antibodies which distinguish between Hb-A and Hb-S or to the monoclonal antibodies themselves. The terms are used interchangeably.

EXAMPLE 3

ELISA Assays With HuS-1

In order to more clearly define the epitopes of these monoclonal antibodies, competitive ELISAs were performed with antigens in solution competing for antibody binding with Hb-S adsorbed on the solid phase. ELISAs were performed according to prior art methods with minor modification in that peroxidase-conjugated goat anti-mouse immunoglobulins were used as the secondary antibodies in the assay and the substrate employed for the peroxidase consisted of a solution of 0.3 mM $H_2O_2$. 0.8 mM 2,2-azino-di-(3-ethylbenzthiazoline) sulfonic acid (ABTS) in 0.1 M sodium citrate buffer, pH 5.5. Antigens attached to microtiter plastic plates were 0.1 ml aliquots of (1) 20 ug/ml of each of VHLTPVEKSAVTYC-BSA, VHLTPEEKSAVTYC-BSA, MBS-BSA, BSA and BTG respectively and (2) 100 ug/ml of each of Hb-S, Hb-AS, and Hb-A. 50 ul of the antibody at various concentrations as shown on the abscissa of FIG. 1, were incubated in each well of a microtiter plate for the ELISA measurements. Concentration of substrate hydrolyzed (as indicated by the increased absorbance at 405 nm) was measured as a function of antibody concentration. FIG. 1a is graph showing the binding of HuS-1 to VHLTPVEKSAVTYC-BSA and VHLTPEEKSAVTYC-BSA, as a plot of antibody concentration vs. relative ELISA response. Slopes of the curves obtained were measured with an automated computer-based enzyme assay system designed at the Lawrence Livermore National Laboratory. Any other method known to those skilled in the art of ELISA measurements would be equally acceptable. The figure shows that HuS-1 binds specifically with VHLTPVEKSAVTYC-BSA at low antibody concentrations, whereas antibody concentrations one hundred times higher were required to bind to the Hb-A analog, VHLTPEEKSAVTYC-BSA. Binding of the antibody to the immunogen VHLTPVEKSAVTYC-BTG was essentially identical to the BSA conjugate. HuS-1 binds very weakly to unsubstituted BSA or BTG or to BSA linked with MBS without the peptide, indicating that the antibody recognizes an epitope that includes only the peptide.

FIG. 1b is another graph showing the binding of HuS-1 with homozygous Hb-SS, Hb-AA and heterozygous Hb-AS in terms of antibody concentration vs. relative ELISA response. It indicates tnat HuS-1 binds to Hb-S less strongly than to the immunogen, but at least one hundred times more strongly than to Hb-A. The small difference in binding to Hb-S from a homozygous SS sample and Hb-AS from a heterozygous AS sample, is attributable to the difference in effective concentration of the Hb-S antigen in the solid phase of the two ELISA reactions. Parallel titrations against Hb-AS from a heterozygous and a 50:50 mixture of homozygous Hb-A and Hb-S gave identical results.

ELISAs were also performed on 24 other human hemoglobin variants that contained single amino acid substitutions at different sites and/or amino acid substitutions that were different from that in Hb-S, and also on seven different primate hemoglobins with amino acid substitutions different from human Hb-S. All these titrations showed reactivity with HuS-1 that was equal to or less than that exhibited by Hb-A.

EXAMPLE 4

ELISA Assays With HuS-2

ELISAs were performed with HuS-2 using exactly the same protocol as described in Example 3 above. Antigens attached to tne microtiter plates were 0.1 ml aliquots of (1) 20 micrograms/ml of each of VHLTPVEKSAVTYC-BSA, VHLTPEEKSAVTYC-BSA, MBS-BSA, BSA and BTG respectively and (2) 100 ug/ml of each of Hb-S, Hb-AS, and Hb-A. Titrations of HuS-2 against twenty four other hemoglobin variants and seven primate hemoglobins showed reactivity that was equal to or less than that exhibited by Hb-A. FIG. 2a is a graph showing the binding of HuS-2 to VHLTPVEKSAVTYC-BSA and VHLTPEEKSAVTYC-BSA, as a plot of antibody concentration vs. relative ELISA response. HuS-2 is seen to exhibit substantial reactivity to the hemoglobin A peptide analog, VHLTPEEKSAVTYC-BSA. As with HuS-1, unsubstituted BSA or BTG shows no reactivity with the antibody, even modified with MBS.

FIG. 2b shows the binding of HuS-2 with homozygous Hb-SS, Hb-AA and heterozygous Hb-AS in terms of antibody vs. relative ELISA response. The reaction of HuS-2 with native hemoglobins displays a higher specificity than might be expected from the peptide titration data. The difference in antibody concentration necessary to bind with Hb-A as compared with Hb-S is at least one hundred fold. These results indicate that the HuS-2 epitope is somewhat different from the HuS-1 epitope. HuS-2 shows only weak specificity for the Hb-S amino acid sequence when peptideprotein conjugates are the antigens, whereas HuS-1 discriminates between the sequences more distinctly. The specificity of the two monoclonal antibodies towards native Hb-S over Hb-A was found to be comparable.

Isotyping, by known methods, of the antibodies produced by HuS-1 indicated them to be IgG2b and tne antibodies produced by HuS-2 to be IgA. Both antibodies were found to contain kappa light chains. Because the two antibodies were of different isotypes, solid-phase, competitive ELISAs, in which the two antibodies were in competition for the epitopes in Hb-S adsorbed on tne solid phase, were performed using a secondary antibody specific for the different heavy chains, thereby to distinguish the differences in their binding affinities and/or specificities to Hb-S. These competitive ELISAs confirmed that the two antibodies do compete for the epitopes on Hb-S and that HuS-2 binds more strongly to Hb-S than HuS-1 by a factor of about ten.

EXAMPLE 5

Flow Cytometry Of Erythrocytes Labeled With HuS-1 And Fluoresceinated Goat Antimouse Immunoglobulin Secondary Antibody Unpurified ascites fluid was diluted one hundred fold in 0.015 M phosphate buffer, pH 7.2, containing 1% BSA, 0.5% NP40, and 0.15 M NaCl. Human erythrocytes were washed and resuspended in a solution containing 0.15 M NaCl, 0.1 M sodium carbonate, 0.1 mM EDTA, 0.01% $NaN_3$, pH 10.3. An equal volume of freshly prepared dimethylsuberimidate at 11 mg/ml was added to the erythrocyte suspension and the mixture incubated at 37° C. for 20 minutes. The solution was washed several times thereafter and the cross-linked erythrocytes were permeabilized by heating to 80° C. for 4 minutes in a water bath, and immediately cooled to 4° C. Three different erythrocyte types, homozygous SS, heterozygous AS and homozygous AA were fixed according to the above methods and added to the antibody solution to yield a final concentration of $10^7$ cells/ml of each type. After incubation of the mixture for 30 minutes at 37° C., the cells were washed and resuspended in fluoresceinated (F/P=3.8) goat anti-mouse immunoglobulin IgG at 20 ug/ml. After another incubation of the mixture for 45 minutes at 37° C., the cells were washed and analyzed by flow cytometry with excitation at 488 nm. Signals were collected and amplified with a logarithmic amplifier such that 7.5 channels on the abscissa equals a doubling of fluorescence intensity. FIG. 3 is a representative flow histogram showing the competitive binding of HuS-1 to Hb-S in the cell types homozygous SS and heterozygous AS in the presence of homozygous AA cells. It shows that homozygous SS cells appear at twice the intensity of heterozygous AS cells, which fluoresce about twenty seven times brighter than homozygous AA cells in the same population. These quantitative immunofluorescence measurements confirm the high specificity of HuS-1 for Hb-S in the fixed erythrocytes. A similar immunofluorescence response was determined for HuS-2 on fixed erythrocytes. These results indicate that these antibodies would be useful as labels in flow cytometric analyses of somatic cell mutations.

EXAMPLE 6

Western blots of HuS-1 and HuS-2

Techniques for western blotting are known to those skilled in the art. The hemoglobins were electrophoresed on a gel slab of Paragon gel, obtained from Beckman Instruments, Palo Alto, Calif., and fixed with acetic acid-methanol. FIG. 4 shows Western blotting pattern of electrophoresis gels immunostained with HuS-1 and HuS-2, for identifying Hb-A and Hb-S. Lanes 1, 4, and 7 shows the gel pattern for Hb-A, lanes 2, 5 and 8 show the electrophoretic pattern of Hb-AS, and lanes 3, 6 and 9 show the electrophoretic pattern of Hb-S. Part of the gel, shown in lanes 1-3, was stained with Serva Blue and the remainder was incubated with HuS-1 (lanes 4-6)or with HuS-2 (lanes 7-9), washed, incubated with peroxidase-conjugated goat anti-mouse immunoglobulins, washed, and incubated with 4-chloro, 1-naphthol substrate.

EXAMPLE 7

Binding Of HuS-1 And HuS-2 To Soluble Peptides

Data obtained from the binding of HuS-1 and HuS-2 to the soluble peptides VHLTPVEKSAVTYC and VHLTPEEKSAVTYC, indicate that when the free peptide is used as the soluble competitor, both monoclonal antibodies bind strongly with VHLTPVEKSAVTYC and only weakly with VHLTPEEKSAVTYC. In addition, the dodecapeptide, VHLTPEEKSAVT, is bound by both monoclonal antibodies just as strongly as is the extended peptide VHLTPEEKSAVTYC.

The foregoing examples indicate that HuS-1 displays about a hundred fold higher affinity for VHLTPVEKSAVTYC-BSA compared with VHLTPEEKSAVTYC-BSA, while HuS-2 binds VHLTPEEKSAVTYC-BSA about a third as strongly as it does to the Hb-S analog, VHLTPEEKSAVTYC-BSA. When the free peptide is used as the soluble competitor, both monoclonal antibodies bind strongly with VHLTPEEKSAVTYC and only weakly with VHLTPEEKSAVTYC. In addition, the dodecapeptide, VHLTPEEKSAVT, is bound by both monoclonal antibodies just as strongly as is the extended peptide VHLTPEEKSAVTYC. These results lead to the conclusion that the epitope for HuS-2 includes the association of peptide with protein, BSA or BTG and that when binding is to native hemoglobin, the peptide portion of the epitope is available, but that the protein portion is not similar to the epitope found in BSA or BTG. Thus, the binding of the monoclonal antibodies to native Hb is not as strong as it is to peptide-BSA conjugate. However, tnere is a large difference in tne binding to Hb-S and Hb-A.

All these examples confirmed that monoclonal antibodies produced by the hybridomas designated as HuS-1 and HuS-2, are highly specific to Hb-S and are able to distinguish Hb-S from Hb-A and from otner hemoglobin variants that differ from each other by a single amino acid residue.

The subject invention thus provides monoclonal antibodies that are able to distinguish between allelic forms of proteins tnat differ by one amino acid residue; specifically, the present monoclonal antibodies distinguish between Hb-S and normal hemoglobin A. The instant invention also provides cell lines which continuously secrete these monoclonal antibodies and methods for their production and use. The monoclonal antibodies of the subject invention bind specifically to Hb-S and are able to distinguish Hb-S from Hb-A on the basis of a single amino acid difference. These monoclonal antibodies are useful for clinical and diagnostic applications where recognition of Hb-S in the presence of an excess of other hemoglobins is desirable. They are contemplated to be useful for monitoring peripheral blood samples for the occurrence of erythrocytes which contain Hb-S in individuals that are Hb-A homozygotes. Since such variations are postulated to be the result of single base substitution mutations in differentiating bone marrow cells, the antibodies of the instant invention are contemplated to be useful in the development of an assay for in vivo somatic cell mutations.

The above embodiments were chosen and described in order to explain best the principles and the practical applications of the subject invention thereby to enable those skilled in the art to utilize the invention in various other embodiments and various modifications as are suitable for the particular use contemplated. The foregoing description of some preferred embodiments of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

We claim:

1. A hybridoma identified as Hu S-1 or HB-8660, which produces monoclonal antibodies which react selectively with human hemoglobin S.

2. A hybridoma identified as Hu S-2 or HB-8661, which produces monoclonal antibodies which react selectively with human hemoglobin S.

3. The antibody produced by the hybridoma of claim 1, which reacts with human hemoglobin S and not with human hemoglobin A.

4. The antibody produced by the hybridoma of claim 2, which reacts with human hemoglobin S and not with human hemoglobin A.

5. A monoclonal antibody produced by a hybridoma selected from the group consisting of HB 8660 and HB 8661.

* * * * *